United States Patent [19]

Kaeding

[11] 4,291,185

[45] Sep. 22, 1981

[54] ALKYLATION OF BENZENE IN PETROLEUM

[75] Inventor: Warren W. Kaeding, Westfield, N.J.

[73] Assignee: Mobil Oil Corporation, New York, N.Y.

[21] Appl. No.: 64,962

[22] Filed: Aug. 8, 1979

Related U.S. Application Data

[63] Continuation-in-part of Ser. No. 969,626, Dec. 14, 1978.

[51] Int. Cl.$^3$ .............................................. C07C 2/68
[52] U.S. Cl. .................................. 585/467; 423/328
[58] Field of Search ................. 260/671, 671 P, 672; 423/328; 585/467

[56] References Cited

U.S. PATENT DOCUMENTS

| | | | |
|---|---|---|---|
| 2,881,227 | 4/1959 | Kiezer | 260/371 |
| 2,904,607 | 9/1959 | Mattox et al. | 585/467 |
| 3,251,897 | 5/1966 | Wise | 585/467 |
| 3,385,906 | 5/1968 | Kaufman | 260/371 |
| 3,702,886 | 11/1972 | Argauer et al. | 423/328 |
| 3,751,504 | 8/1973 | Keown et al. | 585/467 |
| 3,751,506 | 8/1973 | Bumen | 585/467 |
| 3,755,483 | 8/1973 | Burress | 260/671 R |
| 3,767,568 | 10/1973 | Chen | 208/134 |
| 3,776,971 | 12/1973 | Carr et al. | 260/671 P |
| 3,778,415 | 12/1973 | Ko | 260/672 T |
| 3,832,449 | 8/1974 | Rosinski et al. | 252/455 Z |
| 3,843,739 | 10/1974 | Harper et al. | 260/672 T |
| 4,016,245 | 4/1977 | Plank et al. | 423/328 |
| 4,046,859 | 9/1977 | Plank et al. | 423/328 |
| 4,049,737 | 9/1977 | Dwyer et al. | 260/671 P |
| 4,076,842 | 2/1978 | Plank et al. | 252/455 Z |

OTHER PUBLICATIONS

"Operation of the 43-102 Type Industrial Catalytic Cracking Units Using the Zeolite-Containing Catalysts TsEOKAR-2", 1973 Dr. Dorogochinskii et al., Consultants Bureau, Plenum Publishing Co. N.Y. N.Y.

Chemical Abstracts vol. 89 #6023g, Kolesnikov et al., 1978 "Alkylation of Benzene by Propylene and n-butylenes under Pressure in Liquid Phase".

Chemical Abstracts vol. 71 #100994m, Allabbverdieva et al. 1969, "Kinetics of the Alkylation of Benzene by Propylene on Y-Type-Zeolite".

Chemical Abstracts vol. 89 #132224y, Mobil Oil 1977, "Alkylation Transalkylation of Aromatic Hydrocarbons".

Primary Examiner—Winston A. Douglas
Assistant Examiner—Raymond K. Covington
Attorney, Agent, or Firm—C. A. Huggett; R. J. Cier; G. W. Allen

[57] ABSTRACT

A process for selective propylation of the benzene content of hydrocarbon mixtures wherein the mixture is brought into contact with propylene in the presence of a crystalline zeolite catalyst having a silica to alumina mole ratio of at least about 12 and a constraint index of from 1 to 12, to produce isopropylbenzene and diisopropylbenzene. The reaction may be carried out at temperatures of from about 100° C. to the critical temperature of the benzene and at pressures ranging between about $10^5$ N/m$^2$ and $6 \times 10^6$ N/m$^2$.

8 Claims, No Drawings

ALKYLATION OF BENZENE IN PETROLEUM

Cross-References to Related Applications

This is a Continuation-in-part of Ser. No. 969,626, filed 14 Dec. 1978.

BACKGROUND OF THE INVENTION

1. Field of the Invention

The invention disclosed herein relates to a process for selective reaction of benzene by catalytic propylation thereof in the presence of a particular type of crystalline zeolite catalyst.

2. Description of the Prior Art

Alkylation of aromatic hydrocarbons utilizing crystalline zeolite catalysts has heretofore been described. U.S. Pat. No. 2,904,607 to Mattox refers to alkylation of aromatic hydrocarbons with an olefin in the presence of a crystalline metallic aluminosilicate having uniform pore openings of about 6 to 15 Angstrom units. U.S. Pat. No. 3,251,897 to Wise describes alkylation of aromatic hydrocarbons in the presence of X or Y type crystalline zeolites, specifically such type zeolites wherein the cation is rare earth and/or hydrogen. U.S. Pat. No. 3,751,504 to Keown et al and U.S. Pat. No. 3,751,506 to Burress describe vapor phase alkylation of aromatic hydrocarbons with olefins in the presence of a specified type of zeolite catalyst.

U.S. Pat. No. 3,755,483 to Burress discloses vapor phase alkylation of aromatic hydrocarbons in the presence of ZSM-12 zeolite catalyst. The reaction is carried out at room temperature between the critical temperature of the aromatic compound and 482° C. (900° F.). The critical temperature and pressure of benzene are 288.9° C. (552° F.) and 48.6 atmospheres, respectively.

Harper et al have described a catalytic alkylation of benzene with propylene over a crystalline zeolite (Petrochemical Preprints, American Chemical Society, Vol. 22, No. 3, p. 1084, 1977). Extensive kinetic and catalyst aging studies were conducted with a rare earth exchanged Y-type zeolite (REY) catalyst.

SUMMARY OF THE INVENTION

There is disclosed herein a novel process for selectively producing isopropylbenzene by catalytic alkylation of benzene with propylene in the presence of a particular kind of crystalline siliceous zeolite, said zeolite having a silica to alumina mole ratio of at least about 12 and a Constraint Index in the approximate range of 1 to 12. The process may be carried out in both heterogeneous gas/solid and liquid/solid phases at temperatures ranging from about 100° C. to about the critical temperature of the aromatic and, preferably, within the approximate range of 150° C. to 250° C. The catalytic agent particularly preferred comprises the crystalline zeolite designated ZSM-12.

The process has been found useful for effecting propylation of the benzene content of a petroleum refinery reformate fraction which contains, in addition to benzene, close boiling paraffinic components which are normally difficult if not impossible to separate from the benzene. Such utilization of the process of this invention results in the desirable reduction of benzene concentration in the reformate fraction by conversion thereof to isopropylbenzene and diisopropylbenzene, while also providing a relatively low-cost method for producing isopropylbenzene in significant quantities.

A particularly preferred embodiment of this invention involves upgrading the octane rating of motor fuels by converting the benzene content thereof to relatively higher octane number isopropylbenzene.

DESCRIPTION OF SPECIFIC EMBODIMENTS

The crystalline zeolites utilized herein are members of a novel class of zeolitic materials which exhibit unusual porperties. Although these zeolites have unusually low alumina contents, i.e. high silica to alumina mole ratios, they are very active even when the silica to alumina mole ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conductive to long times on stream between regenerations by burning carbonaceous deposits with oxygen-containing gas such as air.

An important characteristic of the crystal structure of this novel class of zeolites is that it provides a selective constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon (or aluminum, etc.) atoms at the centers of the tetrahedra.

The silica to alumina mole ratio referred to may be determined by conventional analysis. This ratio is meant to represent, as closely as possible, the ratio of the rigid anionic framework of the zeolite crystal and to exclude aluminum in the binder or in cationic or other form within the channels. Although zeolites with a silica to alumina ratio of at least 12 are useful, it is preferred in some applications to use zeolites having higher silica/alumina ratios of at least about 30. In addition, zeolites as otherwise characterized herein but which are substantially free of aluminum, i.e. having silica to alumina mole ratios of 1,600 and higher, are found to be useful and even preferable in some instances. Such "high silica" zeolites are intended to be included within this description. The novel class of zeolites, after activation, acquire an intracrystalline sorption capacity for normal hexane which is greater than that for water, i.e. they exhibit "hydrophobic" properties. This hydrophobic character can be used to advantage in some applications.

The novel class of zeolites useful herein have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons and, therefore, it is not the present intention to entirely judge the usefulness of a particular zeolite solely from theoretical structural considerations.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently to gas chromatography, to determine the fraction remaining unchanged for each of the two hydrocarbons.

While the above experimental procedure will enable one to achieve the desired overall conversion of 10 to 60% for most zeolite samples and represents preferred conditions, it may occasionally be necessary to use somewhat more severe conditions for samples of very low activity, such as those having an exceptionally high silica to alumina mole ratio. In those instances, a temperature of up to about 540° C. and a liquid hourly space velocity of less than one, such as 0.1 or less, can be employed in order to achieve a minimum total conversion of about 10%.

The "Constraint Index" is calculated as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (CI) values for some typical materials are:

|  | C.I. |
| --- | --- |
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| TMA Offretite | 3.7 |
| Clinoptilolite | 3.4 |
| Beta | 0.6 |
| H-Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence of absence of binders. Likewise, other variables such as crystal size of the zeolite, the presence of occluded contaminants, etc., may affect the constraint index. Therefore, it will be appreciated that it may be possible to so select test conditions as to establish more than one value in the range of 1 to 12 for the Constraint Index of a particular zeolite. Such a zeolite exhibits the constrained access as herein defined and is to be regarded as having a Constraint Index in the range of 1 to 12. Also contemplated herein as having a Constraint Index in the range of 1 to 12 and therefore within the scope of the defined novel class of highly siliceous zeolites are those zeolites which, when tested under two or more sets of conditions within the above-specified ranges of temperature and conversion, produce a value of the Constraint Index slightly less than 1, e.g. 0.9, or somewhat greater than 12, e.g. 14 or 15, with at least one other value within the range of 1 to 12. Thus, it should be understood that the Constraint Index value as used herein is an inclusive rather than an exclusive value. That is, a crystalline zeolite when identified by any combination of conditions within the testing definition set forth herein as having a Constraint Index in the range of 1 to 12 is intended to be included in the instant novel zeolite definition whether or not the same identical zeolite, when tested under other of the defined conditions, may give a Constraint Index value outside of the range of 1 to 12.

The novel class of zeolites defined herein is exemplified by ZSM-5, ZSM-11, ZSM-12, ZSM-23, ZSM-35, ZSM-38, and other similar materials.

ZSM-5 is described in greater detail in U.S. Pat. No. 3,702,886 and 3,941,871. The entire descriptions contained within those patents, particularly the X-ray diffraction pattern of therein disclosed ZSM-5, are incorporated herein by reference.

ZSM-11 is described in U.S. Pat. No. 3,709,979. That description, and in particular the X-ray diffration pattern of said ZSM-11, is incorporated herein by reference.

ZSM-12 is described in U.S. Pat. No. 3,832,449. That description, and in particular the X-ray diffraction pattern disclosed therein, is incorporated herein by reference.

ZSM-23 is described in U.S. Pat. No. 4,076,842. The entire content thereof, particularly the specification of the X-ray diffraction pattern of the disclosed catalyst, is incorporated herein by reference.

ZSM-35 is described in U.S. Pat. No. 4,016,245. The description of that catalyst, and particularly the X-ray diffraction pattern thereof, is incorporated herein by reference.

ZSM-38 is more particularly described in U.S. Pat. No. 4,046,859. The description of that catalyst, and particularly the specified X-ray diffraction pattern thereof, is incorporated herein by reference.

It is to be understood that by incorporating by reference to foregoing patents to describe examples of specific members of the novel class with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is essentially unbounded. The incorporation of the identified patents should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

The specific zeolites described, when prepared in the presence of organic cations, are substantially catalytically inactive, possibly because the intracrystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-12, ZSM-23, ZSM-35 and ZSM-38, with ZSM-12 being particularly preferred.

In a preferred aspect of this invention, the zeolites hereof are selected as those providing among other things a crystal framework density, in the dry hydrogen form, of not less than about 1.6 grams per cubic centimeter. It has been found that zeolites which satisfy all three of the discussed criteria are most desired for several reasons. When hydrocarbon products or by-products are catalytically formed, for example, such zeolites tend to maximize the production of gasoline boiling range hydrocarbon products. Therefore, the preferred zeolites useful with respect to this invention are those having a Constraint Index as defined above of about 1 to about 12, a silica to alumina mole ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article ZEOLITE STRUCTURE by W. M. Meier. This paper, the entire contents of which are incorporated herein by reference, is included in PROCEEDINGS OF THE CONFERENCE ON MOLECULAR SIEVES, (London, Apr. 1967) published by the Society and Chemical Industry, London, 1968.

When the crystal structure is unkown, the crystal framework density may be determined by classical pyknometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

|  | Void Volume | Framework Density |
| --- | --- | --- |
| Ferrierite | 0.28 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

In practicing a particularly desired chemical conversion process, it may be useful to incorporate the above-described crystalline zeolite with a matrix comprising another material resistant to the temperature and other conditions employed in the process. Such matrix material is useful as a binder and imparts greater resistance to the catalyst for the severe temperature, pressure and reactant feed stream velocity conditions encountered in many cracking processes.

Useful matrix materials include both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

Propylation of benzene in the presence of the above-described catalyst is effected by contact of the benzene or the benzene-containing hydrocarbon mixture, with propylene at a temperature of between about 100° C. and about the critical temperature of benzene and, preferably, between about 150° C. and 250° C. The reaction takes place at atmospheric pressure, but higher pressures, within the approximate range of $10^5$ N/m$^2$ to $6 \times 10^6$ N/m$^2$ (1 atmosphere to 60 atmospheres), may be utilized. The molar ratio of benzene to propylene is preferably within the approximate range of 1.5/1 to 12/1. The reaction may be suitably accomplished utilizing a feed weight hourly space velocity (WHSV) of between about 0.5 and about 100, preferably between about 5 and about 40.

The process of this invention may be conducted with the organic reactants in either the gaseous phase or the liquid phase, or both. Liquid-phase reaction is, however, the most preferred mode for practicing the herein-disclosed invention. It may be carried out as a batch type, semi-continuous or continuous operation utilizing a fixed, fluidized or moving bed catalyst system.

The propylene reactant may be supplied in substantially purified form, in either the gaseous or liquid state. The propylene may contain relatively inert impurities or diluents. Mixtures of propane and propylene, which are commonly available in refineries and in industrial olefin manufacturing facilities, provide desirable sources or propylene for utilization in the process of this invention. A typical example of a propane/propylene stream available in a refinery (presented herein for the purposes of illustration) might have the following composition:

| Compound | Volume % |
| --- | --- |
| Ethane | 0.5 |
| Propane | 57.1 |
| Propylene | 38.4 |
| Butene | 0.7 |
| iso-Butane | 3.1 |
| n-Butane | 0.2 |
| | 100.0 |

While the above stream is considered "typical", the actual composition will, of course, vary. Depending on parameters such as the manufacturing facility, the source of crude oil, the severity of conditions, the design of the purification system, etc., the propylene content of such a stream could vary between approximately 50% and 70%.

Subsequent to use in the present process, the propane component of such a mixed stream may be recovered by conventional means and condensed to liquid form.

In a preferred embodiment of this invention, the above-mentioned benzene-containing hydrocarbon mixture comprises a refinery reformate stream from which one desires to remove some or all of the benzene for environmental or other reasons. With regard to such reformate streams, it should be noted that the liquid product composition from a refinery reforming unit will vary considerably depending on the feed source and the reactor severity, along with a wide variety of other parameters. A reformate product composition obtained from a naphtha feed, under conditions used to maximize the formation of aromatics, is presented below to illustrate a generally typical reformate fraction.

| | Composition of Liquid Product From Reforming | |
| --- | --- | --- |
| Components | Full Range Reformate, wt. % | Aromatic $C_8$ Fraction, wt. % |
| Non-Aromatic | 36 | |
| Benzene | 7 | |
| Toluene | 18 | |
| Ethylbenzene | 3 | 16 |
| 1,2-Dimethylbenzene | 4 | 18 |
| 1,3-Dimethylbenzene | 10 | 47 |
| 1,4-Dimethylbenzene | 4 | 19 |
| Aromatic $C_9^+$ | 18 | |
| | 100 | 100 |

Another preferred embodiment of the novel process disclosed herein involves the upgrading of motor fuels by converting the relatively volatile benzene content thereof to the more desirable isopropylbenzene structure. Besides being less volatile than benzene, which is in itself an important consideration in some applications, isopropylbenzene is known to have a substantially higher blending octane number than does benzene. It has been found that, in the presence of ZSM-12 catalyst, selective propylation of benzene as compared to toluene may be carried out. With respect to motor fuels, such as the so-called "reformate gasoline", this has the significant benefit of converting the benzene content to isopropylbenzene while at the same time minimizing the less desirable conversion of the toluene content to isopropyltoluene (cymene).

The following examples are presented for the purpose of illustrating the process of this invention without imposing undue limitations on the scope or utility thereof.

EXAMPLE 1

A sample of HZSM-12 crystalline zeolite catalyst containing 35 wt.% alumina binder was pressed into wafers, crushed and screened to a uniform particle size of 14 to 20 mesh and placed in a suitable alkylation reactor. To simulate a feed stream comprising a mixture of propane and propylene commonly available in refineries and olefin manufacturing facilities, a mixture of approximately equimolar amounts of propane and propylene were supplied to the alkylation reactor and passed across the HZSM-12 catalyst along with varying amounts of benzene feed. The reaction was carried out at a constant 200° C. and 500 psig and the molar ratio of benzene to propylene was varied from 12.5/1 through 1.81/1. The results are summarized in the following table.

TABLE I

| CONDITIONS OF REACTIONS | | | | |
|---|---|---|---|---|
| Temp. °C. | 200 | 200 | 200 | |
| Press. psig | 500 | 500 | 500 | |
| WHSV Benzene | 14.5 | 14.5 | 14.5 | |
| WHSV Propylene | 0.62 | 1.25 | 1.87 | |
| WHSV Propane | 0.58 | 1.24 | 1.75 | |
| Mole Ratio: | | | | |
| $C_6H_6$ | 12.5 | 6.24 | 4.16 | |
| $C_3H_6$ | 1.0 | 1.0 | 1.0 | |
| $C_3H_8$ | 0.89 | 0.89 | 0.89 | |
| Conversion Wt. % | | | | |
| Benzene | 7.1 | 14.5 | 22.4 | |
| Propylene | 99.8 | 99.9 | 99.7 | |
| Selectivity to Products, Wt. % | | | | |
| Isopropylbenzene | 99.5 | 95.7 | 91.8 | |
| Diisopropylbenzene | 0.4 | 4.1 | 7.2 | |
| n-Propylbenzene | 0 | 0 | 0 | |
| Other | 0.1 | 0.2 | 1.0 | |
| Total | 100.0 | 100.0 | 100.0 | |
| Temp. °C. | 200 | 200 | 200 | 200 |
| Press. psig | 500 | 500 | 500 | 500 |
| WHSV Benzene | 14.5 | 14.5 | 14.5 | 14.5 |
| WHSV Propylene | 2.39 | 3.12 | 3.74 | 4.36 |
| WHSV Propane | 2.33 | 2.91 | 3.49 | 4.07 |
| Mole Ratio: | | | | |
| $C_6H_6$ | 3.12 | 2.50 | 2.11 | 1.81 |
| $C_3H_6$ | 1.0 | 1.0 | 1.0 | 1.0 |
| $C_3H_8$ | 0.89 | 0.89 | 0.89 | 0.89 |
| Conversion, Wt. % | | | | |
| Benzene | 28.4 | 34.3 | 40.0 | 41.3 |
| Propylene | 99.9 | 99.9 | 98.3 | 98.1 |
| Selectivity to Products, Wt. % | | | | |
| Isopropylbenzene | 88.3 | 84.8 | 81.6 | 79.9 |
| Diisopropylbenzene | 10.5 | 13.6 | 16.5 | 17.0 |
| n-Propylbenzene | 0.1 | 0.1 | 0.1 | 0.1 |
| Other | 1.2 | 1.5 | 1.8 | 3.0 |
| Total | 100.0 | 100.0 | 100.0 | 100.0 |

The propane passed through the catalyst bed without reacting and was recovered with the reaction products. Virtually all of the propylene feed was reacted, illustrating the high activity of the HZSM-12 catalyst. The highest selectivity to isopropylbenzene alkylation product was at the 12.5/1 molar feed ratio of benzene to propylene. As the feed ratio was reduced, the yield of diisopropylbenzene increased along with the other (higher boiling) products. The example clearly demonstrates the high activity of the catalyst at relatively low temperature and in a heterogeneous liquid/solid system.

EXAMPLE 2

In a manner similar to that described in Example 1, an approximately equimolar mixture of propane and propylene was used to alkylate benzene at various temperatures in the presence of HZSM-12 catalyst. The pressure was maintained at 500 psig and the molar ratio of benzene to propylene was 6.3/1 with the feed WHSV of 14.6 for benzene, 1.25 for propylene and 1.16 for propane. Table II summarizes the results of these reactions.

TABLE II

| CONDITIONS OF REACTION | | | |
|---|---|---|---|
| Temp. °C. | 150 | 175 | 200 |
| Press. psig | 500 | 500 | 500 |
| WHSV Benzene | 14.6 | 14.6 | 14.6 |
| WHSV Propylene | 1.25 | 1.25 | 1.25 |
| WHSV Propane | 1.16 | 1.16 | 1.16 |
| Mole Ratio: | | | |
| $C_6H_6$ | 6.3 | 6.3 | 6.3 |
| $C_3H_6$ | 1.0 | 1.0 | 1.0 |
| $C_3H_8$ | 0.89 | 0.89 | 0.89 |
| Conversion Wt. % | | | |
| Benzene | 11.5 | 12.9 | 14.5 |
| Propylene | 99.8 | 99.5 | 99.9 |
| Selectivity to Products, Wt. % | | | |
| Isopropylbenzene | 96.9 | 96.2 | 95.7 |
| Diisopropylbenzene | 2.8 | 3.6 | 4.2 |
| n-Propylbenzene | 0 | 0 | 0 |
| Other | 0.3 | 0.2 | 0.1 |
| Total | 100.0 | 100.0 | 100.0 |
| Temp. °C. | 225 | 250 | 300 |
| Press. psig | 500 | 500 | 500 |
| WHSV Benzene | 14.6 | 14.6 | 14.6 |
| WHSV Propylene | 1.25 | 1.25 | 1.25 |
| WHSV Propane | 1.16 | 1.16 | 1.16 |
| Mole Ratio: | | | |
| $C_6H_6$ | 6.3 | 6.3 | 6.3 |
| $C_3H_6$ | 1.0 | 1.0 | 1.0 |
| $C_3H_8$ | 0.89 | 0.89 | 0.89 |
| Conversion Wt. % | | | |
| Benzene | 15.1 | 15.2 | 14.9 |
| Propylene | 99.9 | 99.9 | 99.9 |
| Selectivity to Products, Wt. % | | | |
| Isopropylbenzene | 93.8 | 93.1 | 80.7 |
| Diisopropylbenzene | 5.7 | 6.0 | 4.2 |
| n-Propylbenzene | 0.2 | 0.7 | 13.8 |
| Other | 0.3 | 0.2 | 1.3 |
| Total | 100.0 | 100.0 | 100.0 |

In every case, virtually all of the propylene in the feed mixture was converted to alkylation products. Significant amounts of n-propylbenzene appeared at 300° C., representing the upper practical temperature limit of the operation under this combination of operating conditions. The results of this and the foregoing Example 1 indicate that the relatively low cost refinery and olefin plant propane/propylene streams can be desirably utilized in this process for a direct reaction of benzene to alkylation product.

EXAMPLE 3

A typical benzene containing refinery reformate fraction, including components with boiling points similar to that of benzene, was simulated by preparing a 30 wt. % solution of benzene in heptane. This solution, together with a 50/50 propane/propylene mixture, was passed over a catalyst bed comprising HZSM-12 catalyst. The reaction was carried out at 500 psig and temperatures ranging from 150° C. through 250° C. The results are summarized in Table III below.

TABLE III

| CONDITIONS OF REACTION | | | | |
|---|---|---|---|---|
| Temp. °C. | 150 | 200 | 225 | 250 |
| Pressure, psig | 500 | 500 | 500 | 500 |
| WHSV: | | | | |
| Benzene | 3.6 | 3.7 | 3.6 | 3.6 |
| Propylene | 2.1 | 2.2 | 2.2 | 2.2 |
| Propane | 1.9 | 2.0 | 2.0 | 2.0 |
| Heptane | 8.4 | 8.6 | 8.4 | 8.4 |
| Mole Ratio: | | | | |
| Benzene | 0.93 | 0.92 | 0.92 | 0.89 |
| Propylene | 1.0 | 1.0 | 1.0 | 1.0 |
| Propane | 0.89 | 0.89 | 0.89 | 0.89 |
| Heptane | 1.71 | 1.69 | 1.64 | 1.64 |
| Conversion, Wt. %: | | | | |
| Benzene | 13.3 | 49.7 | 55.6 | 57.6 |
| Propylene | 61.2 | 97.7 | 96.0 | 97.5 |
| Selectivity to Products, Wt. %: | | | | |
| Isopropylbenzene | 75.8 | 65.9 | 61.2 | 59.4 |
| Diisopropylbenzene | 4.5 | 25.8 | 31.9 | 33.3 |
| Other aromatics | 4.0 | 3.2 | 2.8 | 3.4 |
| $C_5 + C_6$ | 14.9 | 5.0 | 4.0 | 3.4 |
| Light gas | 0.8 | 0.1 | 0.1 | 0.5 |
| Total | 100.0 | 100.0 | 100.0 | 100.0 |
| Benzene, wt. %: | | | | |
| In | 22.5 | 22.4 | 22.2 | 22.2 |
| Out | 20.7 | 11.1 | 9.4 | 8.8 |
| Reduction, % | 8.0 | 50.1 | 57.7 | 60.4 |

The propane and heptane diluents did not react under the conditions of the reaction and were recovered unchanged. As will be seen from the data in the table, there was significant reaction of the benzene constituent with the propylene feed. The reaction products were substantially mono-and diisopropylbenzenes with minor amounts of other aromatics. The isopropylbenzene alkylation products may subsequently be recovered and purified by conventional technology or, if desired, may remain in the reformate product.

EXAMPLE 4

To illustrate another embodiment of the invention, the benzene concentration of a commercially available unleaded gasoline sample was reduced as follows: 100 ml (73.4 g) of gasoline, 10 ml (6.1 g) of propylene and 4 g of powdered ZSM-12 zeolite were sealed in a 300 ml stirred autoclave. The contents were heated for various time/temperature intervals and samples of the liquid product were withdrawn and analyzed by gas-liquid chromatography G.C.). An additional 10 ml (6.1 g) of propylene was added after Run #2. The reaction conditions and reduction in benzene content (as determined by the reduction in G.C. peak area for benzene) are shown in Table IV.

TABLE IV

| Catalyst: ZSM-12 Run No. | SM[a] | 1 | 2[b] | 3 | 4 |
|---|---|---|---|---|---|
| Temp., °C. | — | 100 | 150 | 200 | 200 |
| Time, total hrs. | — | .5 | 1.0 | 1.5 | 2.0 |
| Pressure, psig | — | 230–225 | 315–300 | 600–480 | 480–390 |
| Normalized Benzene Peak area, % | 2.40 | 2.26 | 2.12 | 1.87 | 1.78 |
| Benzene Conc. % of original | 100 | 96.6 | 90.6 | 79.9 | 73.9 |

[a]Starting Material - peak area for benzene was 2.40%
[b]Added 10 ml (6.1g) of propylene between Runs 2 and 3

EXAMPLE 5

In a manner similar to that described in Example 4, 100 ml (73.4 g) of Reformate Gasoline, a hydrocarbon mixture rich in aromatics, was combined with 10 ml (6.2 g) of propylene and 4 g of powdered ZSM-12 catalyst in the autoclave. Samples were withdrawn and analyzed at various time periods. Results are summarized in Table V. A rapid reaction occurred which preferentially removed benzene by alkylation to produce isopropylbenzene. An additional 10 ml (6.1 g) of propylene was added between Runs 3 and 4, resulting in further reductions in benzene concentration. Primary reaction products were isopropylbenzene and isopropyltoluene. Over 70% of the benzene was removed by the second treatment. The propylene fed was consumed to produce liquid alkylation product with relatively high octane value.

TABLE V

| Catalyst ZSM-12 Run No. | Reformate Gasoline | 1 | 2 | 3 | 4[a] | 5 | 6 |
|---|---|---|---|---|---|---|---|
| Time Run, hrs. | 13 | .25 | .50 | 1.50 | 1.75 | 2.0 | 3.0 |
| Pressure, psig | — | 410–280 | 280–250 | 250–240 | 390–250 | 250–220 | 220–210 |
| Composition, wt % | | | | | | | |
| Benzene | 14.2 | 7.8 | 6.6 | 6.3 | 4.5 | 3.8 | 3.7 |
| Toluene | 29.1 | 20.3 | 17.8 | 17.0 | 12.3 | 11.2 | 9.9 |
| Ethylbenzene | .6 | .5 | .4 | .4 | .3 | .3 | .3 |
| Dimethylbenzene | 1.5 | 1.3 | 1.3 | 1.7 | 1.2 | 2.0 | 1.3 |
| $C_3H_6$ (added) | — | 1.9 | .3 | .3 | .4 | .3 | .3 |
| $C_5$ | 15.7 | 13.3 | 13.3 | 13.1 | 12.7 | 11.6 | 12.2 |
| $C_6$ | 20.8 | 18.4 | 18.4 | 17.9 | 17.7 | 16.4 | 16.8 |
| $C_7^+$ | 18.1 | 17.9 | 18.4 | 17.6 | 17.3 | 17.3 | 17.4 |
| (Products) | | | | | | | |
| Isopropylbenzene | 0 | 6.7 | 8.1 | 8.2 | 9.0 | 9.5 | 9.6 |
| Isopropyltoluene | 0 | 10.0 | 12.6 | 13.4 | 17.5 | 19.6 | 20.0 |
| $C_{10}^+$ | 0 | 1.9 | 2.8 | 4.1 | 7.1 | 8.0 | 8.5 |
| Total | 100.0 | 100.0 | 100.0 | 100.0 | 100.0 | 100.0 | 100.0 |
| Reduction in Benzene, wt % | — | 45.4 | 53.9 | 55.4 | 68.1 | 72.9 | 74.0 |

TABLE V-continued

| Catalyst ZSM-12 Run No. | Reformate Gasoline | 1 | 2 | 3 | 4(a) | 5 | 6 |
|---|---|---|---|---|---|---|---|
| Toluene, wt % | — | 30.3 | 38.9 | 41.7 | 57.6 | 61.5 | 66.1 |

(a) added 10ml (6.1g) of propylene between Runs 3 and 4.

EXAMPLE 6

To illustrate another method for reducing the concentration of benzene in hydrocarbon mixtures by selective alkylation with propylene to produce alkylbenzenes, 100 ml (73.4 g) of reformate gasoline and 4 g of powdered ZSM-12 zeolite catalyst were placed in the autoclave and heated to 200° C. Propylene was pumped into the reactor continuously at a rate of 10 ml (6.1 g) per hour. Samples were withdrawn periodically and analyzed to determine the concentration of benzene. Results are summarized in Table VI. By this method, about 85% of the benzene was removed by an alkylation process over a 3-hour period.

EXAMPLE 7

In a manner similar to that described in Example 6, 4 g of powdered HZSM-5 zeolite was used as the catalyst. Results are summarized in Table VII. Benzene was alkylated selectively during the first 1.75 hours of operation by comparison with toluene, but the selectivity deteriorated thereafter.

TABLE VII

| Catalyst: HZSM-5 Run No. | Reformate Gasoline | 1 | 2 | 3 | 4 |
|---|---|---|---|---|---|
| Time Run, Hrs. | | .5 | 1.0 | 1.75 | 3.25 |
| Pressure, psig | | 180–195 | 200–225 | 260–280 | 445–425 |
| Temp., °C. | | 200 | 200 | 200 | 300 |
| Liquid Composition, Wt % | | | | | |
| Benzene | 14.2 | 13.4 | 13.0 | 11.6 | 7.2 |
| Toluene | 29.1 | 29.5 | 27.8 | 24.1 | 12.6 |
| Ethylbenzene | .6 | .6 | .6 | .6 | .4 |
| Dimethylbenzene | 1.5 | 1.8 | 1.6 | 1.5 | 1.4 |
| $C_3H_6$ | 0 | .2 | .6 | 1.1 | .5 |
| $C_5$ | 15.7 | 14.2 | 13.7 | 11.8 | 14.2 |
| $C_6$ | 20.8 | 19.8 | 19.7 | 17.4 | 17.4 |
| $C_7$ | 18.1 | 19.0 | 18.4 | 17.3 | 19.5 |
| (Products) | | | | | |
| Isopropylbenzene | 0 | .4 | 1.0 | 2.2 | 6.2 |
| Isopropyltoluene | 0 | 1.0 | 3.3 | 7.4 | 16.4 |
| $C_{10}^+$ | 0 | .1 | .1 | 5.0 | 4.2 |
| Total | 100.0 | 100.0 | 100.0 | 100.0 | 100.0 |
| Reduction in | | | | | |
| Benzene, wt % | 0 | 5.6 | 8.5 | 18.3 | 49.3 |
| Toluene, wt % | 0 | 0 | 4.5 | 17.2 | 56.7 |

EXAMPLE 8

In a manner similar to that described in Examples 6 and 7, 4 g of powdered HSZM-11 zeolite was used as the catalyst. Results are summarized in Table VIII. Benzene was selectively alkylated, compared with toluene, during the first half hour of operation. After this, toluene was preferentially alkylated.

TABLE VI

| Catalyst: ZSM-12 Run No. | Reformate Gasoline | 1 | 2 | 3 | 4 |
|---|---|---|---|---|---|
| Time Run, hrs. | | .50 | 1.0 | 2.0 | 3.0 |
| Pressure, psig | | 180 | 170–180 | 165–160 | 160–170 |
| Temp., °C. | | 200 | 200 | 200 | 200 |
| Liquid Composition, Wt % | | | | | |
| Benzene | 14.2 | 12.9 | 9.7 | 4.0 | 2.1 |
| Toluene | 29.1 | 28.9 | 23.9 | 13.9 | 7.8 |
| Ethylbenzene | .6 | .6 | .5 | .4 | .3 |
| Dimethylbenzene | 1.5 | 1.7 | 1.8 | 1.5 | 1.1 |
| $C_3H_6$ (added) | — | .1 | .1 | .2 | .7 |
| $C_5$ | 15.7 | 13.9 | 10.0 | 10.6 | 10.3 |
| $C_6$ | 20.8 | 19.9 | 19.5 | 15.5 | 15.1 |
| $C_7^+$ | 18.1 | 18.5 | 18.5 | 16.0 | 16.7 |
| (Products) | | | | | |
| Isopropylbenzene | 0 | 1.3 | 6.3 | 11.2 | 9.3 |
| Isopropyltoluene | 0 | 1.5 | 7.9 | 20.5 | 26.2 |
| $C_{10}^+$ | 0 | .7 | 1.8 | 6.2 | 10.4 |
| Total | 100.0 | 100.0 | 100.0 | 100.0 | 100.0 |
| Reduction in | | | | | |
| Benzene, wt % | — | 8.9 | 31.8 | 72.2 | 84.7 |
| Toluene, wt % | — | .5 | 17.9 | 52.1 | 73.1 |

TABLE VIII

| Catalyst: HZSM-11 | | Reformate | | | |
|---|---|---|---|---|---|
| Run No. | | Gasoline | 1 | 2 | 3 |
| Time Run, Hrs. | | — | .5 | 1.0 | 3 |
| Pressure, psig | | — | 200–190 | 190–195 | 195–180 |
| Temp., °C. | | — | 200 | 200 | 200 |
| Liquid Composition, Wt % | | | | | |
| Benzene | | 14.2 | 12.9 | 10.3 | 5.1 |
| Toluene | | 29.1 | 27.7 | 20.0 | 6.9 |
| Ethylbenzene | | .6 | .6 | .5 | .2 |
| Dimethylbenzene | | 1.5 | 1.7 | 1.3 | .6 |
| $C_3H_6$ | | 0 | .2 | .3 | .4 |
| $C_5$ | | 15.7 | 13.5 | 12.0 | 10.7 |
| $C_6$ | | 20.8 | 19.1 | 17.2 | 15.5 |
| $C_7$ | | 18.1 | 18.0 | 26.1 | 16.0 |
| (Products) | | | | | |
| Isopropylbenzene | | 0 | 1.3 | 2.7 | 7.7 |
| Isopropyltoluene | | 0 | 3.6 | 7.9 | 21.9 |
| $C_{10}^+$ | | 0 | 1.4 | 1.7 | 15.0 |
| | Total | 100.0 | 100.0 | 100.0 | 100.0 |
| Reduction in | | | | | |
| Benzene, wt % | | 0 | 9.2 | 27.5 | 64.1 |
| Toluene, wt % | | 0 | 4.8 | 31.3 | 76.3 |

EXAMPLE 9

In a manner similar to that described in Examples 6 and 7, 4 g of powdered HZSM-4 zeolite was used. Results are summarized in Table IX. In contrast to all previous runs, toluene was preferentially alkylated, by comparison with benzene, under all conditions of reactions tested.

TABLE IX

| Catalyst: HZSM-4 | | Reformate | | | |
|---|---|---|---|---|---|
| Run No. | | Gasoline | 1 | 2 | 3 |
| Time Run, Hrs. | | — | .5 | 1.0 | 2.0 |
| Pressure, psig | | — | 190–180 | 180–160 | 150–125 |
| Temp., °C. | | — | 200 | 200 | 200 |
| Liquid Composition, Wt % | | | | | |
| Benzene | | 14.2 | 12.9 | 10.5 | 6.4 |
| Toluene | | 29.1 | 24.9 | 17.1 | 6.5 |
| Ethylbenzene | | .6 | .6 | .4 | .2 |
| Dimethylbenzene | | 1.5 | 1.5 | 1.1 | .5 |
| $C_3H_6$ | | 0 | .1 | .1 | .1 |
| $C_5$ | | 15.7 | 14.2 | 13.4 | 12.7 |
| $C_6$ | | 20.8 | 19.6 | 19.0 | 17.9 |
| $C_7$ | | 18.1 | 17.7 | 18.2 | 16.4 |
| (Products) | | | | | |
| Isopropylbenzene | | 0 | 1.5 | 3.7 | 6.5 |
| Isopropyltoluene | | 0 | 5.7 | 13.0 | 19.6 |
| $C_{10}^+$ | | 0 | 1.3 | 3.5 | 13.2 |
| | Total | 100.0 | 100.0 | 100.0 | 100.0 |
| Reduction in | | | | | |
| Benzene, wt % | | 0 | 9.2 | 26.1 | 54.9 |
| Toluene, wt % | | 0 | 14.4 | 41.2 | 77.7 |

EXAMPLE 10

To illustrate a continuous mode of operation for selectively removing benzene from a hydrocarbon mixture by alkylation with propylene, a synthetic mixture of reformate gasoline was prepared. It was composed of 13.6% (by weight) benzene, 29.1% toluene and 57.3% n-heptane. The ratio and amount of benzene and toluene were similar to that observed for the actual reformate gasoline used in Examples 6–9. The synthetic reformate gasoline and propylene were mixed and pumped over 9.3 grams of microcrystalline HZSM-12 catalyst (which containted 35% alumina binder) in the form of 1/16"extruded particles, packed in a metal, fixed bed reactor. In Run 1, Table X, the feed was composed of 11.8 (wt) % benzene, 25.2% toluene, 49.7% n-heptane and 13.3% propylene at a weight hourly space velocity of 11.8. The benzene/toluene/$C_7$/$C_3H_4$ molar ratio was 0.55/1.00/1.83/1.16. The products were condensed and collected for a 1-hour period of operation and were primarily a liquid with a relatively small amount of gas. Results are summarized in Table X. It can be seen that benzene was alkylated selectively under all conditions of reaction to significantly reduce the benzene concentration in the liquid product. Furthermore, the propylene consumed was converted primarily to a liquid hydrocarbon.

TABLE X

| Catalyst: HZSM-12-Extrudate | | | | |
|---|---|---|---|---|
| Sample No. | Feed | 1 | 2 | 3 |
| Time Run, Hrs. (Total) | — | 1 | 2 | 3 |
| Pressure, psig | — | 500 | 500 | 500 |
| Temp., °C. | — | 200 | 150 | 200 |
| WHSV | | 11.8 | 12.5 | 21.8 |
| Composition, Wt % | | | | |
| Benzene | 11.8 | 5.6 | 8.8 | 8.3 |
| Toluene | 25.2 | 17.3 | 22.0 | 23.2 |
| $C_3H_6$ | 13.3 | .3 | 5.8 | .9 |
| $C_6$ | — | — | .2 | — |

TABLE X-continued

Catalyst: HZSM-12-Extrudate

| Sample No. | Feed | 1 | 2 | 3 |
|---|---|---|---|---|
| $C_7$ (Products) | 49.7 | 49.4 | 49.3 | 52.2 |
| Isopropylbenzene | | 7.2 | 3.7 | 5.6 |
| Isopropyltoluene | | 13.3 | 6.7 | 7.8 |
| Diisopropylbenzene | | 4.3 | 2.4 | 1.6 |
| $C_{11}{}^+$ | | 2.6 | 1.1 | .4 |
| Total | 100.0 | 100.0 | 100.0 | 100.0 |
| Reduction in | | | | |
| Benzene, wt % | 0 | 52.5 | 25.4 | 29.7 |
| Toluene, wt % | 0 | 31.3 | 12.7 | 7.9 |

It is to be understood that the foregoing description is intended to be merely illustrative of certain preferred embodiments of this invention, of which many variations may be made by those skilled in the art within the scope of the following claims without departing from the spirit thereof.

What is claimed is:

1. A process for the selective reaction of benzene relative to toluene in hydrocarbon mixtures comprising benzene, toluene and other aliphatic and aromatic hydrocarbons, said selective conversion process comprising contacting said hydrocarbon mixture with propylene, at a temperature of between about 100° C. and the critical temperature of the benzene reactant at a pressure of between about $10^5$ N/m$^2$ and about $6 \times 10^6$ N/m$^2$, in the presence of a selective catalyst comprising ZSM-12 zeolites.

2. A process as defined in claim 1 wherein said propylene is contained in a mixture comprising both propane and propylene, said propane remaining substantially unreacted and being recovered at the end of said process.

3. A process as defined in claim 1 wherein said temperature is between about 150° C. and about 250° C.

4. A process as defined in claim 1 wherein said zeolite is combined with a binder therefor.

5. A process for upgrading motor fuels containing benzene therein, said process comprising contacting said motor fuel with propylene, at a temperature of between about 100° C. and the critical temperature of said benzene and a pressure of between about $10^5$ N/m$^2$ and $6 \times 10^6$ N/m$^2$, in the presence of a crystalline zeolite comprising ZSM-12.

6. A process as defined in claim 5 wherein said temperature is between about 150° C. and about 250° C.

7. A process as defined in claim 5 wherein said zeolite is combined with a binder therefor.

8. A process as defined in claim 5 wherein said propylene is contained in a mixture comprising both propane and propylene.

* * * * *

UNITED STATES PATENT AND TRADEMARK OFFICE
CERTIFICATE OF CORRECTION

PATENT NO. : 4,291185

DATED : September 22, 1981

INVENTOR(S) : Warren W. Kaeding

It is certified that error appears in the above—identified patent and that said Letters Patent is hereby corrected as shown below:

Column 7, line 46    "1.5/1" should be --0.5/1--

Column 7, line 64    "or" should read --of--

Column 12, line 6    Insert --(-- before "G.C."

Column 12, lines 33-34    "6.2g)" should read --(6.1g)--

Column 12, line 51    delete "13" in first column of Table V entitled "Reformate Gasoline".

Column 14, line 34    ".1" should be --.3-- in Column "2" of Table VII

Signed and Sealed this

Second Day of February 1982

[SEAL]

Attest:

GERALD J. MOSSINGHOFF

Attesting Officer    Commissioner of Patents and Trademarks